United States Patent
McNeff et al.

(10) Patent No.: US 8,697,893 B2
(45) Date of Patent: Apr. 15, 2014

(54) SYSTEMS AND METHODS FOR PRODUCING FUELS AND FUEL PRECURSORS FROM CARBOHYDRATES

(75) Inventors: Clayton V. McNeff, Andover, MN (US); Daniel T. Nowlan, Hugo, MN (US)

(73) Assignee: Sartec Corporation, Anoka, MN (US)

( * ) Notice: Subject to any disclaimer, the term of this patent is extended or adjusted under 35 U.S.C. 154(b) by 339 days.

(21) Appl. No.: 12/645,119

(22) Filed: Dec. 22, 2009

(65) Prior Publication Data
US 2010/0191004 A1 Jul. 29, 2010

Related U.S. Application Data

(60) Provisional application No. 61/139,684, filed on Dec. 22, 2008.

(51) Int. Cl.
*C07D 307/02* (2006.01)

(52) U.S. Cl.
USPC ...................................................... 549/488

(58) Field of Classification Search
USPC ...................................................... 549/488
See application file for complete search history.

(56) References Cited

U.S. PATENT DOCUMENTS

| | | | |
|---|---|---|---|
| 1,873,537 A | 8/1932 | Brown et al. |
| 2,014,408 A | 9/1935 | Woodhouse |
| 2,851,468 A | 9/1958 | Snyder |
| 4,098,809 A | 7/1978 | Pagani |
| 4,138,336 A | 2/1979 | Mendel et al. |
| 4,225,630 A | 9/1980 | Pitchon |
| 4,242,455 A | 12/1980 | Muller et al. |
| 4,425,433 A | 1/1984 | Neves |
| 4,808,526 A | 2/1989 | Lawford |
| 4,885,405 A | 12/1989 | Dornhagen et al. |
| 4,911,941 A | 3/1990 | Katz et al. |
| 4,950,812 A | 8/1990 | Jacobs et al. |
| 5,108,597 A | 4/1992 | Funkenbusch et al. |
| 5,182,016 A | 1/1993 | Funkenbusch et al. |
| 5,231,017 A | 7/1993 | Lantero et al. |
| 5,254,262 A | 10/1993 | Funkenbusch et al. |
| 5,271,833 A | 12/1993 | Funkenbusch et al. |
| 5,346,619 A | 9/1994 | Funkenbusch et al. |
| 5,527,970 A | 6/1996 | Hwan et al. |
| 5,540,834 A | 7/1996 | Carr et al. |
| 5,651,953 A | 7/1997 | Yokoyama et al. |
| 5,972,118 A | 10/1999 | Hester et al. |
| 6,441,202 B1 | 8/2002 | Lightner |
| 6,666,074 B2 | 12/2003 | Gerner et al. |
| 7,135,308 B1 | 11/2006 | Bush |
| 2003/0032819 A1 | 2/2003 | Lightner |
| 2003/0199049 A1 | 10/2003 | Nguyen et al. |
| 2003/0199149 A1 | 10/2003 | Lee et al. |
| 2005/0112739 A1 | 5/2005 | Golubkov |
| 2005/0118409 A1 | 6/2005 | McNeff et al. |
| 2006/0135823 A1 | 6/2006 | Jun et al. |
| 2007/0225383 A1 | 9/2007 | Cortright et al. |
| 2008/0194811 A1 | 8/2008 | McNeff |
| 2008/0319236 A1 | 12/2008 | McNeff et al. |

FOREIGN PATENT DOCUMENTS

| | | |
|---|---|---|
| DE | 102004056786 | 7/2005 |
| EP | 0169953 A1 | 2/1986 |
| EP | 0506428 A1 | 9/1992 |
| EP | 1396483 A1 | 3/2004 |
| JP | 2000355692 | 12/2000 |
| JP | 2006129735 | 5/2006 |
| WO | WO-99/50213 A1 | 10/1999 |
| WO | WO-2006041253 | 4/2006 |
| WO | WO-2007146636 A1 | 12/2007 |
| WO | WO-2008101007 | 8/2008 |
| WO | WO-2009003039 | 12/2008 |
| WO | WO-2010075437 A3 | 7/2010 |

OTHER PUBLICATIONS

Watanabe et al. Carbohydrate Research 340 (2005) 1925-1930.*
Becker et al. Green Chemistry, 2003, 5, 280-284.*
Cottier et al. Heterocyclic Chemistry, 1991, 2, 233-248.*
Dias et al. Journal of Catalysis, 2005, 229, 414-423.*
Chheda et al. Catalysis Today 2007, 123 59-70.*
Su, Yu et al., "Single step conversion of cellulose to 5-hydroxymethylfurfural (HMF), a versatile platform chemical", Applied Catalysis A: General, 361 Apr. 9, 2009, 117-122.
"Examination Notification Art. 94(3)", for European Application No. 08729762.8, corresponding to U.S. Appl. No. 60/889,730, mailed May 30, 2011, 3 Pgs.
"Final Office Action", Citation mailed Mar. 26, 2012 in co pending U.S. Appl. No. 12/030,649, "Catalysts and Methods for Complex Carbohydrate Hydrolysis" (13pages).
"Non Final Office Action", mailed Sep. 6, 2011 in co pending U.S. Appl. No. 12/030,649, "Catalysts and Methods for Complex Carbohydrate Hydrolysis" (12 pages).
PCT Notification Concerning Transmittal of International Preliminary Report on Patentability from International Application No. PCT/US2009/069280, corresponding to U.S. Appl. No. 12/645,119, mailed Jul. 7, 2011, pp. 1-12.
"EP First Communication", European Examination Report, from the European Patent Office in EP Patent Application No. 08771929.0, corresponding to U.S. Appl. No. 12/149,175, mailed Jun. 1, 2010, (pp. 1-2).

(Continued)

*Primary Examiner* — Nizal Chandrakumar
(74) *Attorney, Agent, or Firm* — Pauly, Devries Smith & Deffner, LLC.

(57) ABSTRACT

The present invention relates to systems and methods for producing fuels and fuel precursors from carbohydrates. In an embodiment the invention includes a method of producing 5-hydroxymethylfurfural (HMF), including contacting a saccharide with a metal oxide catalyst at a temperature of greater than about 100 degrees Celsius. In an embodiment the invention includes a method of producing a biofuel including contacting a saccharide with a metal oxide catalyst at a temperature of greater than about 100 degrees Celsius. Other embodiments are also described herein.

8 Claims, 4 Drawing Sheets

(56) References Cited

OTHER PUBLICATIONS

"File History", File History for co-pending U.S. Appl. No. 12/030,649, "*Catalysts and Methods for Complex Carbohydrate Hydrolysis*," Filed Feb. 13, 2008 (127 pages).

"File History", for co-pending U.S. Appl. No. 12/146,175, "*Catalysts, Systems and Methods for Ether Synthesis*," Filed Jun. 25, 2008 (121 pages).

Unknown, "New Process Makes Diesel Fuel and Industrial Chemicals from Simple Sugar", *College of Engineering University of Wisconsin-Madison*, http://www.engr.wisc.edu/news/headlines/2006/Jun29a.html 1 of 3 Jun. 18, 2008 9:28 AM Jun. 29, 2006.

"PCT International Search Report and Written Opinion", from International Application No. PCT/US2008,068188, corresponding to U.S. Appl. No. 12/146,175, mailed Sep. 3, 2008, pp. 1-15.

"PCT International Search Report and Written Opinion", from International Application No. PCT/US2009069280, corresponding to U.S. Appl. No. 12/645,119, mailed Sep. 13, 2010, pp. 1-20.

"PCT International Search Report and Written Opinion", PCT International Search Report and Written Opinion from International Application No. PCT/US2008/053844, corresponding to U.S. Appl. No. 12/030,649, mailed Aug. 6, 2008, pp. 1-14.

"PCT Notification Concerning Transmittal of International Preliminary Report on Patentability", from International Application No. PCT/US2008/053844, corresponding to U.S. Appl. No. 12/030,649, mailed Aug. 27, 2000.

"PCT Notification Concerning Transmittal of International Preliminary Report on Patentability", from International Application No. PCT/US2008/068188, corresponding to U.S. Appl. No. 12/146,175, mailed Jan. 14, 2010, pp. 1-5.

Annen, M. J. "Development of Porous Zirconia Spheres by Polymerization-Induced Colloid Aggregation—Effect of Polymerization Rate", *Journal of Material Science* 1994, 29: 6123-6130.

DME Project at Air Products, "Liquid Phase Dimethyl Ether Demonstration in the LaPorte Alternative Fuels Development Unit", *Air Products and Chemicals, Inc.*, Allentown, Pennsylvania (Jan. 2001).

Kittelson, "Biofuels for Engines", *Third Annual IREE Research Symposium University of Minnesota, Twin Cities Campus* (Nov. 28, 2006).

Miller, Dennis J. "Catalysis for Biorenewables Conversion", *National Science Foundation Workshop Report* www.egr.msu.edu/apps/nsfworkshop Apr. 2004, 1-63.

Moreau, C. "Applied Catalysis A:General", vol. 145, No. 1-2, XP002454168 tables 1,3 1996, pp. 211-224.

Perlack, Robert D. "Biomass as Feedstock for Bioenergy and Bioproducts Industry: Technical Feasibility of a Billion-Ton Annual Supply", *U.S. Department of Agriculture* Apr. 2005, 1-78.

Petkewich, Rachel "Sweet Routes To Sustainability: Catalytic reactions converts sugars from biomass into renewable fuel and feedstock", *Chemical & Engineering News*, http://pubs.acs.org/cen/news/85/i26/8526notw1.html Jun. 25, 2007, vol. 85, No. 26, p. 8.

Qi., X. "Catalysis Communications", vol. 9, No. 13, XP022824415 p. 2245, paragraph 2.2; tables 1-3, table 2 Jul. 20, 2008, pp. 2244-2249.

Robichaud, "An Improved Oil Emulsion Synthesis Method for Large, Porous Zirconia Particles for Packed-or Fluidized-Bed Protein Chromatography", *Sep. Science Technol.*, 32(15):2547-2559 (1997).

Sassi, "Methanol to hydrocarbon catalysis on sulfated zirconia proceeds through a hydrocarbon-pool mechanism", *Catalysis Letters*, 81(1-2):101-105 (2002).

Watanabe, Masaru "Catalytic Hydrogen Generation from Biomass (Glucose and Cellulose) with $ZrO_2$ in Supercritical Water", *Biomass and Bioenergy* 2002, 22, 405-410.

Xu, M. "Synthesis of dimethyl ether (DME) from methanol over solid-acid catalysts", *Applied Catalysis A: General, Elsevier, Science, Amsterdam, NL* vol. 149, No. 2 Feb. 6, 1997, 289-301 Pgs.

Yalpani, M. "Alterations of Polysaccharide Intergrity and Electrochemical Modifications", *Polysaccharides, Syntheses, Modifications and Structure* Jan. 1, 1988, 370-4004.

"Non-Final Office Action", mailed Aug. 2, 2012 in co-pending U.S. Appl. No. 12/146,175, "Catalysts, Systems and Methods for Ether Synthesis," (16 pages).

"Non-Final Office Action", mailed Oct. 2, 2012 in U.S. Appl. No. 12/030,649, "Catalysts and Methods for Complex Carbohydrate Hydrolysis" (11 pages).

"Mexico Office Action", from MX Application No. MX/a/2009/008683, mailed Oct. 10, 2012 (pp. 1-3) Including English translation.

"Response to Non-Final Office Action", dated Aug. 2, 2012 in U.S. Appl. No. 12/146,175 mailed Jan. 2, 2013, 7 pages.

Final Office Action, from U.S. Appl. No. 12/146,175, mailed Mar. 20, 2013, 12 pgs.

\* cited by examiner

SYSTEMS AND METHODS FOR PRODUCING FUELS AND FUEL PRECURSORS FROM CARBOHYDRATES

This application claims the benefit of U.S. Provisional Application No. 61/139,684, filed Dec. 22, 2008, the content of which is herein incorporated by reference in its entirety.

FIELD OF THE INVENTION

The present invention relates to systems and methods for producing fuels and fuel precursors from carbohydrates.

BACKGROUND OF THE INVENTION

Carbohydrates include a group of organic compounds based on the general formula $C_x(H_2O)_y$. The group specifically includes monosaccharides, disaccharides, oligosaccharides, polysaccharides (sometimes called "glycans"), and their derivatives. Monosaccharides can include hexoses and pentoses. A hexose is a monosaccharide with six carbon atoms. A pentose is a monosaccharide with five carbon atoms.

Carbohydrates are molecules of fundamental importance to living organisms as many carbohydrates serve as a chemical store of energy for living organisms. For example, glucose is a monosaccharide found in fruits, honey, and the blood of many animals that can be readily metabolized by many organisms to provide energy. Glucose also has many industrial uses, including as a feedstock for microbial ethanol production.

Carbohydrates can be chemically converted into higher value molecules. For example, carbohydrates can be converted into fuels or precursors used to produce other compounds. As one example, hexoses can be chemically converted into the hexose derivative 5-hydroxymethylfurfural (HMF). HMF can be valuable as an intermediate in the production of other compounds. For example, HMF can be chemically converted into DMF (2,5-dimethylfuran), an important potential biofuel. As another example, pentoses can be chemically converted into the pentose derivative 2-furaldehyde. However, existing methods for these chemical processes can be inefficient, expensive, slow, and non-scalable.

SUMMARY OF THE INVENTION

The present invention relates to systems and methods for producing fuels and fuel precursors from carbohydrates. In an embodiment the invention includes a method of producing 5-hydroxymethylfurfural (HMF), including contacting a saccharide with a metal oxide catalyst at a temperature of greater than about 100 degrees Celsius.

In an embodiment the invention includes a method of producing an ether-acetal product from a hexose derivative including contacting a hexose derivative and an alcohol with a metal oxide catalyst at a temperature of greater than about 100 degrees Celsius.

In an embodiment the invention includes a method of producing an ether-acetal product from a hexose including contacting a hexose with a first metal oxide catalyst at a temperature of greater than about 100 degrees Celsius to produce a hexose derivative; and then contacting the hexose derivative and an alcohol with a second metal oxide catalyst at a temperature of greater than about 100 degrees Celsius.

In an embodiment the invention includes a method of producing a diether product from a hexose derivative including selectively reducing the hexose derivative to form a first reaction product; and contacting the first reaction product and an alcohol with a metal oxide catalyst at a temperature of greater than about 100 degrees Celsius.

In an embodiment the invention includes a method of producing a diether product from a hexose including contacting a hexose with a first metal oxide catalyst at a temperature of greater than about 100 degrees Celsius to produce a hexose derivative; selectively reducing the hexose derivative to form a first reaction product; and contacting the first reaction product and an alcohol with a second metal oxide catalyst at a temperature of greater than about 100 degrees Celsius.

In an embodiment the invention includes a method of producing a diester product from a hexose derivative including selectively oxidizing the hexose derivative to form a first reaction product; and contacting the first reaction product and an alcohol with a metal oxide catalyst at a temperature of greater than about 100 degrees Celsius.

In an embodiment the invention includes a method of producing a diester product from a hexose including contacting a hexose with a first metal oxide catalyst at a temperature of greater than about 100 degrees Celsius to produce a hexose derivative; selectively oxidizing the hexose derivative to form a first reaction product; and contacting the first reaction product and an alcohol with a second metal oxide catalyst at a temperature of greater than about 100 degrees Celsius.

In an embodiment the invention includes a method of producing a diacetal product from a hexose derivative including selectively oxidizing the hexose derivative to form a first reaction product; and contacting the first reaction product and an alcohol with a metal oxide catalyst at a temperature of greater than about 100 degrees Celsius.

In an embodiment the invention includes a method of producing a diacetal product from a hexose including contacting a hexose with a first metal oxide catalyst at a temperature of greater than about 100 degrees Celsius to produce a hexose derivative; selectively oxidizing the hexose derivative to form a first reaction product; and contacting the first reaction product and an alcohol with a second metal oxide catalyst at a temperature of greater than about 100 degrees Celsius.

In an embodiment the invention includes a method of producing an acetal product from a pentose derivative including contacting a pentose derivative and an alcohol with a metal oxide catalyst at a temperature of greater than about 100 degrees Celsius.

In an embodiment the invention includes a method of producing an acetal product from a pentose including contacting a pentose with a first metal oxide catalyst at a temperature of greater than about 100 degrees Celsius to produce a pentose derivative; and contacting the pentose derivative and an alcohol with a second metal oxide catalyst at a temperature of greater than about 100 degrees Celsius.

In an embodiment the invention includes a method of producing an ether product from a pentose derivative including selectively reducing the pentose derivative to form a first reaction product; and contacting the first reaction product and an alcohol with a metal oxide catalyst at a temperature of greater than about 100 degrees Celsius.

In an embodiment the invention includes a method of producing an ether product from a pentose including contacting a pentose with a first metal oxide catalyst at a temperature of greater than about 100 degrees Celsius to produce a pentose derivative; selectively reducing the pentose derivative to form a first reaction product; and contacting the first reaction product and an alcohol with a second metal oxide catalyst at a temperature of greater than about 100 degrees Celsius.

In an embodiment the invention includes a method of producing an ester product from a pentose derivative including selectively oxidizing the pentose derivative to form a first reaction product; and contacting the first reaction product and an alcohol with a metal oxide catalyst at a temperature of greater than about 100 degrees Celsius.

In an embodiment the invention includes a method of producing an ester product from a pentose including contacting a pentose with a first metal oxide catalyst at a temperature of greater than about 100 degrees Celsius to produce a pentose derivative; selectively oxidizing the pentose derivative to form a first reaction product; and contacting the first reaction product and an alcohol with a second metal oxide catalyst at a temperature of greater than about 100 degrees Celsius.

In an embodiment, the invention includes a method of producing a biofuel including contacting a saccharide with a metal oxide catalyst at a temperature of greater than about 100 degrees Celsius.

In an embodiment, the invention includes an apparatus for producing 5-hydroxymethylfurfural (HMF) including a feedstock tank comprising a saccharide feedstock; a reactor vessel in fluid communication with the feedstock tank; a plurality of metal oxide catalyst particles disposed within the reactor vessel; a heating element; and
a back pressure regulator in fluid communication with the reactor vessel.

The above summary of the present invention is not intended to describe each discussed embodiment of the present invention. This is the purpose of the figures and the detailed description that follows.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

As disclosed herein, it has been discovered that certain metal oxide catalysts can be used in order to catalyze the reaction of carbohydrates, such as monosaccharides, to produce pentose and hexose derivatives. In some embodiments, these pentose and hexose derivatives can be further converted into other chemical compounds of interest. As such, in accordance with embodiments herein, feedstocks such as glucose, sucrose, fructose, and the like can be turned into value-added products and product precursors through chemical reactions including metal oxide catalyzed reactions. It will be appreciated that various embodiments of methods herein can be executed as continuous flow processes.

Exemplary hexoses can include allose, altrose, glucose, mannose, gulose, idose, galactose, talose, psicose, fructose, sorbose, and tagatose. In a particular embodiment, the hexose is selected from glucose, mannose, galactose, fructose, or combinations thereof.

Exemplary pentoses can include ribose, arabinose, xylose, lyxose, ribulose, and xylulose. In a particular embodiment, the pentose is selected from ribose, arabinose, xylose, and ribulose.

In some embodiments, saccharides including more than one saccharide group such as disaccharides, oligosaccharides, and polysaccharides can be subjected to a first hydrolysis step producing monosaccharides that can then be further processed according to various methods disclosed herein. For example, sucrose can be hydrolyzed into fructose and glucose before being converted into hexose derivatives according to methods disclosed herein. As another example, cellulose can be hydrolyzed before being processed according to methods disclosed herein. Hydrolysis steps can be catalyzed by metal oxide catalysts as described herein. In some embodiments, hydrolysis steps can be performed at an elevated temperature. For example, in some embodiments hydrolysis steps can be performed at a temperature of greater than about 100 degrees Celsius.

Degradation of Hexoses and Pentoses into Hexose Derivatives and Pentose Derivatives In an embodiment, the invention includes a method of converting hexoses and/or pentoses into hexose derivatives and pentose derivatives respectively. As one specific example, a hexose can be chemically converted into the hexose derivative 5-hydroxymethylfurfural (HMF). As another specific example, a pentose can be chemically converted into the pentose derivative 2-furaldehyde. The method can include contacting a monosaccharide (such as a hexose or pentose) with a metal oxide catalyst at temperature of greater than about 100 degrees Celsius. Exemplary reaction conditions are described in greater detail below.

In some embodiments, various non-reactants can be used as part of a reaction mixture during the step of converting hexoses and/or pentoses into hexose derivatives and pentose derivatives respectively. Non-reactants can include, but are not limited to, solvents. In some embodiments, a biphasic solvent system can be used, including a reactive phase and an extraction phase. For example, in some embodiments the reaction mixture can include a first aqueous phase and a second phase at least partially immiscible with the aqueous phase. In some embodiments, the second phase can be a butanol phase. While not intending to be bound by theory, it is believed that the biphasic system can be advantageous in some cases because reaction products (such as HMF, in the case of a hexose reaction) can be transferred out of the aqueous phase and into the extraction phase after formation, thus preventing possible decomposition of the hexose derivative.

Conversion of Hexose Derivatives and Pentose Derivatives

In various embodiments, hexose derivatives and/or pentose derivatives can be converted into higher value products. For example, hexose derivatives can be converted into ether-acetals, diethers, diesters, and/or diacetals. As a further example, pentose derivatives can be converted into acetals, ethers, and/or esters.

Ether-Acetal Formation from Hexose Derivatives

In accordance with various embodiments herein, hexose derivatives can be converted into various value added chemical compounds. For example, with reference to FIG. 1, hexose derivatives can be converted into ether-acetal products. As a specific example 5-HMF can be reacted with a minimum three equivalents of alcohol at high temperature using metal oxide catalysts as described herein to simultaneously etherify the alcohol and affect acetal formation at the aldehyde group, providing an ether-acetal product. It is believed that these products can display increased hydrophobicity while being highly oxygenated, rendering this class of molecules useful as fuel additives or biomass derived fuel surrogates.

Diether Formation from Hexose Derivatives

Figure 1:
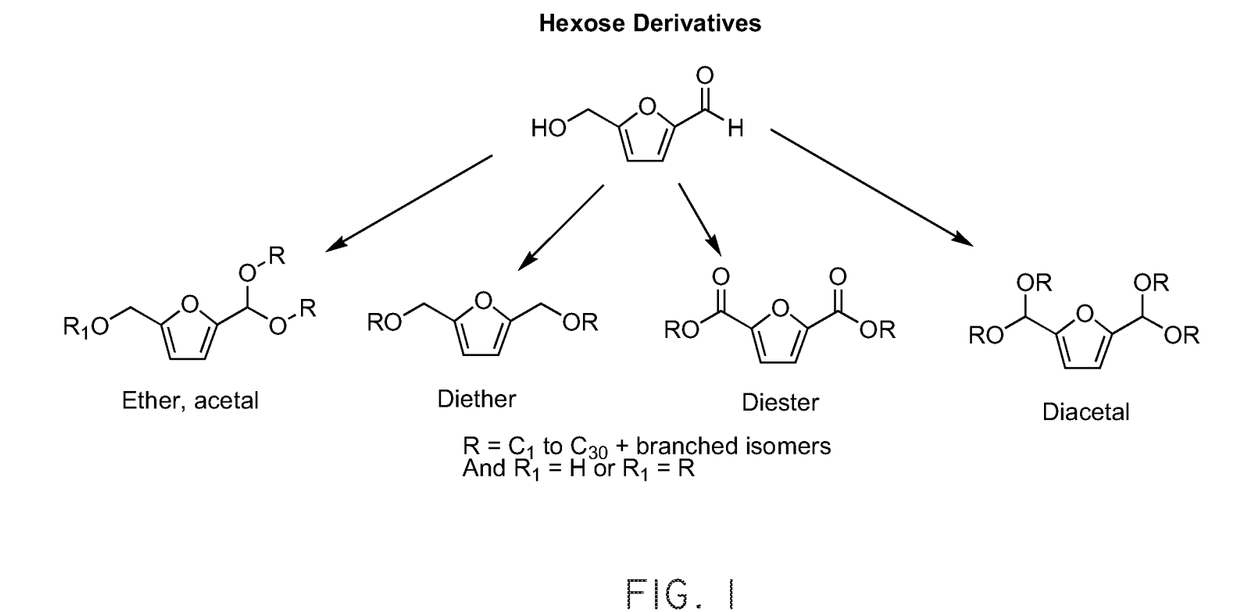
FIG. 1 is a schematic diagram of the conversion of an exemplary hexose derivative (5-HMF) into various other chemical compounds.

As another example, with reference to FIG. 1, hexose derivatives can be converted into diether products. As a first step, a hexose derivative such as 5-HMF can be selectively hydrogenated at the aldehyde functionality to provide 2,5-(dihydroxymethyl)furan. This selective hydrogenation step can be performed according to various methods known to those of skill in the art. 2,5-(dihydroxymethyl)furan is a useful monomer in the formation of biodegradable polymers and a fine chemical for organic synthesis. As a second step, 2,5-(dihydroxymethyl)furan may further be reacted with two equivalents of an alcohol at high temperature using metal oxide catalysts as described herein to etherify both alcohol moieties and provide a diether as the final product.

Depending on the alcohol selected this class of compounds can display increased hydrophobicity and sufficient energy density to be useful as fuel additives or fuel surrogates. It is also recognized that the incomplete reaction to form the monoether may occur and provide a useful product as well. Depending on the structure of the alcohol used a molecule with a non-polar tail and polar head can be formed.

Diester Formation from Hexose Derivatives

As another example, with reference to FIG. 1, hexose derivatives can be converted into diester products. As a first step, 5-HMF can be selectively and fully oxidized at the alcohol and aldehyde functionalities to provide furan-2,5-dicarboxylic acid. Various methods of performing this step are known to those of skill in the art. As a second step, furan-2,5-dicarboxylic acid can be reacted with a minimum of two equivalents of an alcohol at high temperature using metal oxide catalysts to produce a diester product.

Depending on the alcohol selected this class of compounds can display increased hydrophobicity and sufficient energy density to be useful as fuel additives or fuel surrogates. It is also recognized that whether through an incomplete reaction or the intentional addition of a substoichiometric amount of alcohol the formation of an acid-ester will occur, which can be a class of compounds demonstrating increased hydrophobicity and sufficient energy density to be useful as fuel additives or fuel surrogates. Also, depending on the structure of the alcohol used, a molecule with a non-polar tail and polar head can be formed.

Diacetal Formation from Hexose Derivatives

As another example, with reference to FIG. 1, hexose derivatives can be converted into diacetal products. As a first step, 5-HMF can be selectively and partially oxidized at the alcoholic functionality to provide 2,5-diformylfuran. This step can be formed through various methods known to those of skill in the art. As a second step, 2,5-diformylfuran can be reacted with a minimum of four equivalents of alcohol or two equivalents of a polyol at high temperature using metal oxide catalysts as described herein to produce a diacetal product.

Depending on the alcohol selected this class of compounds can display increased hydrophobicity and sufficient energy density to be useful as fuel additives or fuel surrogates. It is also recognized that whether through an incomplete reaction or the intentional addition of a substoichiometric amount of alcohol the formation of an acetal-aldehyde will occur, which can be a class of compounds demonstrating increased hydrophobicity and sufficient energy density to be useful as fuel additives or fuel surrogates.

Acetal Formation from Pentose Derivatives

Figure 2:
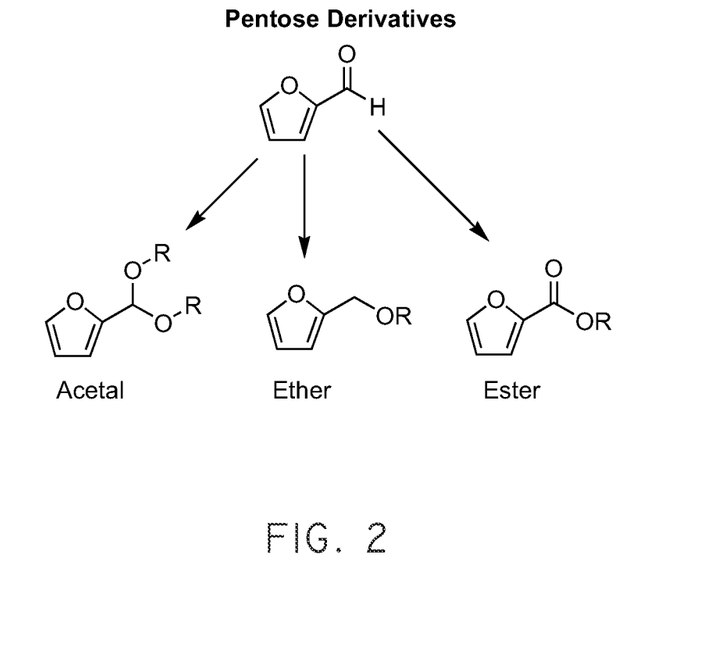
FIG. 2 is a schematic diagram of the conversion of an exemplary pentose derivative (2-furaldehyde) into various other chemical compounds.

With reference to FIG. 2, products resulting from pentose degradation, such as 2-furaldehyde, can be reacted with a minimum of two equivalents of an alcohol or one equivalent of a polyol at high temperature using metal oxide catalysts as described herein to produce an acetal product. These products can display increased hydrophobicity and sufficient energy density to be useful as fuel additives or fuel surrogates.

Ether Formation from Pentose Derivatives

As another example, with reference to FIG. 2, pentose derivatives can be converted into ether products. As a first step, a pentose derivative such as 2-furaldehyde can be selectively hydrogenated at the aldehyde functionality to provide 2-hydroxymethylfuran. There are many ways to accomplish this transformation known to those skilled in the art. As a second step, 2-hydroxymethylfuran can be further reacted with one equivalent of an alcohol at high temperature using metal oxide catalysts as described herein to etherify the alcohol moiety and provide an ether as the final product.

Depending on the alcohol selected this class of compounds can display increased hydrophobicity and sufficient energy density to be useful as fuel additives or fuel surrogates.

Ester Formation from Pentose Derivatives

As another example, with reference to FIG. 2, pentose derivatives can be converted into ester products. As a first step a pentose derivative, such as 2-furaldehyde can be selectively oxidized at the aldehyde functionality to provide 2-furanoic acid. There are many ways to accomplish this transformation known to those of skill in the art. As a second step, 2-furanoic acid can be further reacted with one equivalent of an alcohol at high temperature using metal oxide catalysts as described herein to esterify the carboxylic acid functionality and provide an ester as the final product. Depending on the alcohol selected this class of compounds can display increased hydrophobicity and sufficient energy density to be useful as fuel additives or fuel surrogates.

Metal Oxide Catalysts

Metal oxide catalysts used with embodiments of the invention can include metal oxides with surfaces including Lewis acid sites, Lewis base sites, Brönsted base sites, and Brönsted acid sites. By definition, a Lewis acid is an electron pair acceptor and a Lewis base in an electron pair donor. A Brönsted base is a proton acceptor and a Brönsted acid is a proton donor. Metal oxide catalysts of the invention can specifically include zirconia, alumina, titania and hafnia. Metal oxide catalysts of the invention can also include silica clad with a metal oxide selected from the group consisting of zirconia, alumina, titania, hafnia, zinc oxide, copper oxide, magnesium oxide and iron oxide. In some embodiments, the metal oxides are used in a substantially pure form, unmixed with other metal oxides. However, metal oxide catalysts of the invention can also include mixtures of metal oxides, such as mixtures of metal oxides including zirconia, alumina, titania and/or hafnia. Of the various metal oxides that can be used with embodiments of the invention, zirconia, titania and hafnia can be advantageous as they are very chemically and thermally stable and can withstand very high temperatures and pressures as well as extremes in pH.

Metal oxides of the invention can include metal oxide particles clad with carbon. Carbon clad metal oxide particles can be made using various techniques such as the procedures described in U.S. Pat. Nos. 5,108,597; 5,254,262; 5,346,619; 5,271,833; and 5,182,016, the contents of which are herein incorporated by reference. Carbon cladding on metal oxide particles can render the surface of the particles more hydrophobic.

Metal oxides of the invention can also include polymer coated metal oxides. By way of example, metal oxides of the invention can include a metal oxide coated with polybutadiene (PBD). Polymer coated metal oxide particles can be made using various techniques such as the procedure described in Example 1 of U.S. Pub. Pat. App. No. 2005/0118409, the contents of which are herein incorporated by reference. Polymer coatings on metal oxide particles can render the surface of the particles more hydrophobic.

Metal oxide catalysts of the invention can be made in various ways. As one example, a colloidal dispersion of zirconium dioxide can be spray dried to produce aggregated zirconium dioxide particles. Colloidal dispersions of zirconium dioxide are commercially available from Nyacol Nano Technologies, Inc., Ashland, Mass. The average diameter of particles produced using a spray drying technique can be varied by changing the spray drying conditions. Examples of spray drying techniques are described in U.S. Pat. No. 4,138,336 and U.S. Pat. No. 5,108,597, the contents of both of which are herein incorporated by reference. It will be appreciated that other methods can also be used to create metal oxide particles. One example is an oil emulsion technique as described in Robichaud et al., Technical Note, "An Improved Oil Emulsion Synthesis Method for Large, Porous Zirconia Particles for Packed- or Fluidized-Bed Protein Chromatography," Sep. Sci. Technol. 32, 2547-59 (1997). A second example is the formation of metal oxide particles by polymer induced colloidal aggregation as described in M. J. Annen, R. Kizhappali, P. W. Carr, and A. McCormick, "Development of Porous Zirconia Spheres by Polymerization-Induced Colloid Aggregation-Effect of Polymerization Rate," J. Mater. Sci. 29, 6123-30 (1994). A polymer induced colloidal aggregation technique is also described in U.S. Pat. No. 5,540,834, the contents of which are herein incorporated by reference.

Metal oxide catalysts used in embodiments of the invention can be sintered by heating them in a furnace or other heating device at a relatively high temperature. In some embodiments, the metal oxide is sintered at a temperature of about 160° C. or greater. In some embodiments, the metal oxide is sintered at a temperature of about 400° C. or greater. In some embodiments, the metal oxide is sintered at a temperature of about 600° C. or greater. Sintering can be done for various amounts of time depending on the desired effect. Sintering can make metal oxide catalysts more durable. In some embodiments, the metal oxide is sintered for more than about 30 minutes. In some embodiments, the metal oxide is sintered for more than about 3 hours. However, sintering also reduces the surface area. In some embodiments, the metal oxide is sintered for less than about 1 week.

In some embodiments, the metal oxide catalyst is in the form of particles. Particles within a desired size range can be specifically selected for use as a catalyst. For example, particles can be sorted by size using techniques such as air classification, elutriation, settling fractionation, or mechanical screening. In some embodiments, the size of the particles is greater than about 0.2 μm. In some embodiments, the size range selected is from about 0.2 μm to about 1 mm. In some embodiments, the size range selected is from about 1 μm to about 100 μm. In some embodiments, the size range selected is from about 25 μm to about 80 μm.

In some embodiments, the particles are zirconium dioxide and the average size selected is about 25 μm. In some embodiments, the particles are titanium dioxide and the average size selected is about 80 μm.

In some embodiments, metal oxide particles used with embodiments of the invention are porous. By way of example, in some embodiments the metal oxide particles can have an average pore size of about 30 angstroms to about 2000 angstroms. However, in other embodiments, metal oxide particles used are non-porous.

The physical properties of a porous metal oxide can be quantitatively described in various ways such as by surface area, pore volume, porosity, and pore diameter. In some embodiments, metal oxide catalysts of the invention can have a surface area of between about 1 and about 200 m$^2$/gram. Pore volume refers to the proportion of the total volume taken up by pores in a material per weight amount of the material. In some embodiments, metal oxide catalysts of the invention can have a pore volume of between about 0.01 cm$^3$/g and about 2 cm$^3$/g. Porosity refers to the proportion within a total volume that is taken up by pores. As such, if the total volume of a particle is 1 cm$^3$ and it has a porosity of 0.5, then the volume taken up by pores within the total volume is 0.5 cm$^3$. In some embodiments, metal oxide catalysts of the invention can have a porosity of between about 0 and about 0.8. In some embodiments, metal oxide catalysts of the invention can have a porosity of between about 0.3 and 0.6.

Metal oxide particles used with embodiments of the invention can have various shapes. By way of example, in some embodiments the metal oxide can be in the form of spherules. In other embodiments, the metal oxide can be a monolith. In some embodiments, the metal oxide can have an irregular shape.

The Lewis acid sites on metal oxides of the invention can interact with Lewis basic compounds. Thus, Lewis basic compounds can be bonded to the surface of metal oxides of the invention. Lewis basic compounds of the invention can include anions formed from the dissociation of acids such as hydrobromic acid, hydrochloric acid, hydroiodic acid, nitric acid, sulfuric acid, perchloric acid, boric acid, chloric acid, phosphoric acid, pyrophosphoric acid, chromic acid, permanganic acid, phytic acid and ethylenediamine tetramethyl phosphonic acid (EDTPA), and the like. Lewis basic compounds of the invention can also include hydroxide ion as formed from the dissociation of bases such as sodium hydroxide, potassium hydroxide, lithium hydroxide and the like.

The anion of an acid can be bonded to a metal oxide of the invention by refluxing the metal oxide in an acid solution. By way of example, metal oxide particles can be refluxed in a solution of sulfuric acid. Alternatively, the anion formed from dissociation of a base, such as the hydroxide ion formed from dissociation of sodium hydroxide, can be bonded to a metal oxide by refluxing in a base solution. By way of example, metal oxide particles can be refluxed in a solution of sodium hydroxide. The base or acid modification can be achieved under exposure to the acid or base in either batch or continuous flow conditions when disposed in a reactor housing at elevated temperature and pressure to speed up the adsorption/chemical reaction process. In some embodiments, fluoride ion, such as formed by the dissociation of sodium fluoride, can be bonded to the particles.

In some embodiments, metal oxide particles can be packed into a housing, such as a column. Disposing metal oxide particles in a housing is one approach to facilitating continuous flow processes. Many different techniques may be used for packing the metal oxide particles into a housing. The specific technique used may depend on factors such as the average particle size, the type of housing used, etc. Generally speaking, particles with an average size of about 1-20 microns can be packed under pressure and particles with an average size larger than 20 microns can be packed by dry-packing/tapping methods or by low pressure slurry packing. In some embodiments, the metal oxide particles of the invention can be impregnated into a membrane, such as a PTFE membrane.

However, in some embodiments, metal oxide catalysts used with embodiments of the invention are not in particulate form. For example, a layer of a metal oxide can be disposed on a substrate in order to form a catalyst used with embodiments of the invention. The substrate can be a surface that is configured to contact the feedstock during processing. In one approach, a metal oxide catalyst can be disposed as a layer over a surface of a reactor that contacts the feedstock. Alternatively, the metal oxide catalyst can be embedded as a particulate in the surface of an element that is configured to contact the feedstock during processing.

In various embodiments, a reactor system is included. The reactor system can include various components. For example, the reactor system can include, but is not limited to, the components shown in FIG. 3 and described below.

Reaction Conditions

In some embodiments, the reaction temperature is about 100° Celsius or higher. In some embodiments, the reaction temperature is about 150° Celsius or higher. In some embodiments, the reaction temperature is about 200° Celsius or higher. In some embodiments, the reaction temperature is about 300° Celsius or higher. In some embodiments, the reaction temperature is about 350° Celsius or higher. In some embodiments, the reaction temperature is less than about 280° Celsius. In some embodiments, the reaction temperature is between about 260° Celsius and about 280° Celsius.

The reaction mixture may be passed over the metal oxide catalyst for a length of time sufficient for the reaction to reach a desired level of completion. This will, in turn, depend on various factors including the temperature of the reaction, the chemical nature of the catalyst, the surface area of the catalyst, the contact time with the catalyst and the like. In an embodiment, the contact time is between about 0.1 seconds and 10 hours. In an embodiment, the contact time is between about 0.1 seconds and 2 hours. In an embodiment, the contact time is between about 1 second and 20 minutes. In an embodiment, the contact time is between about 1 minute and 5 minutes. In an embodiment, the contact time is between about 1 minute and about 3 minutes. In some embodiments, the contact time is about 2 minutes.

In some embodiments, the reaction mixture is kept under pressure during the reaction in order to prevent components of the reaction mixture from vaporizing. The reactor housing can be configured to withstand the pressure under which the reaction mixture is kept. In addition, a backpressure regulator can be used to maintain a desired pressure. A desirable pressure for the reactor can be estimated with the aid of the Clausius-Clapeyron equation. Specifically, the Clausius-Clapeyron equation can be used to estimate the vapor pressures of a liquid. The Clausius-Clapeyron equation is as follows:

$$\ln\left(\frac{P_1}{P_2}\right) = \frac{\Delta H_{vap}}{R}\left(\frac{1}{T_2} - \frac{1}{T_1}\right)$$

wherein $\Delta H_{vap}$=is the enthalpy of vaporization; $P_1$ is the vapor pressure of a liquid at temperature $T_1$; $P_2$ is the vapor pressure of a liquid at temperature $T_2$, and R is the ideal gas constant.

In an embodiment, the pressure inside the housing is greater than the vapor pressures of any of the components of the reaction mixture. In an embodiment, the pressure is greater than about 500 psi. In an embodiment, the pressure is greater than about 800 psi. In an embodiment, the pressure is greater than about 1000 psi. In an embodiment, the pressure is greater than about 1500 psi. In an embodiment, the pressure is greater than about 2000 psi. In an embodiment, the pressure is greater than about 3000 psi. In an embodiment, the pressure is greater than about 3000 psi. In an embodiment, the pressure is greater than about 4000 psi. In an embodiment, the pressure is greater than about 5000 psi.

Solvents

Exemplary alcohols used with embodiments herein can include aliphatic, aromatic, and alicyclic alcohols. In some embodiments, alcohols can include C1-C30 alcohols (alcohols with one to thirty carbon atoms). In some embodiments, alcohols can include C1-C6 alkyl alcohols. Alcohols used herein can be mono-functional or multi-functional (e.g., one alcohol group or multiple alcohol group). Exemplary alcohols can specifically include methanol, ethanol, propanol, isopropyl alcohol, butanol, ethylene glycol, benzyl alcohol and the like. In some embodiments, the alcohol is selected from the group consisting of methanol, ethanol, and butanol.

Other solvents can include other organic compounds. In some embodiments, solvents can include organic liquids that form a phase distinct from water at room temperature and pressure. Exemplary solvents can include, but are not limited to, ketones. By way of example, one exemplary solvent is methyl isobutyl ketone.

The present invention may be better understood with reference to the following examples. These examples are intended to be representative of specific embodiments of the invention, and are not intended as limiting the scope of the invention.

EXAMPLES

Example 1

Formation of Titania Reactor Columns

Titania (80 micron average particle size, 300 Å average pore diameter) particles were obtained from ZirChrom Separations (Anoka, Minn.). Particles were packed at ZirChrom Separations (Anoka, Minn.) into a reactor column using a downward slurried high-pressure packing station (Alltech Associates, Deerfield, Ill.). The particles were packed into all-stainless steel column hardware obtained from Isolation Technologies (Hopedale, Mass.). The reactor was outfitted with 2-micron stainless steel fits.

The reactor column had dimensions of 0.46 cm i.d.×15 cm length. A slurry was first formed by adding the titania particles to HPLC-grade methanol. Reactor packing pressures of 7,000 PSI was used with methanol as the pusher solvent. The reactor was allowed to pack and compress. The high pressure packing pump from Haskel (Burbank, Calif.) was then shut off and the reactor was allowed to slowly bleed off pressure while remaining attached to the packing apparatus. When the pressure had been fully released, the column was disconnected from the apparatus and the frit and end fitting were attached to the inlet to complete construction of the reactor column.

Example 2

Reactor System Design

Figure 3:
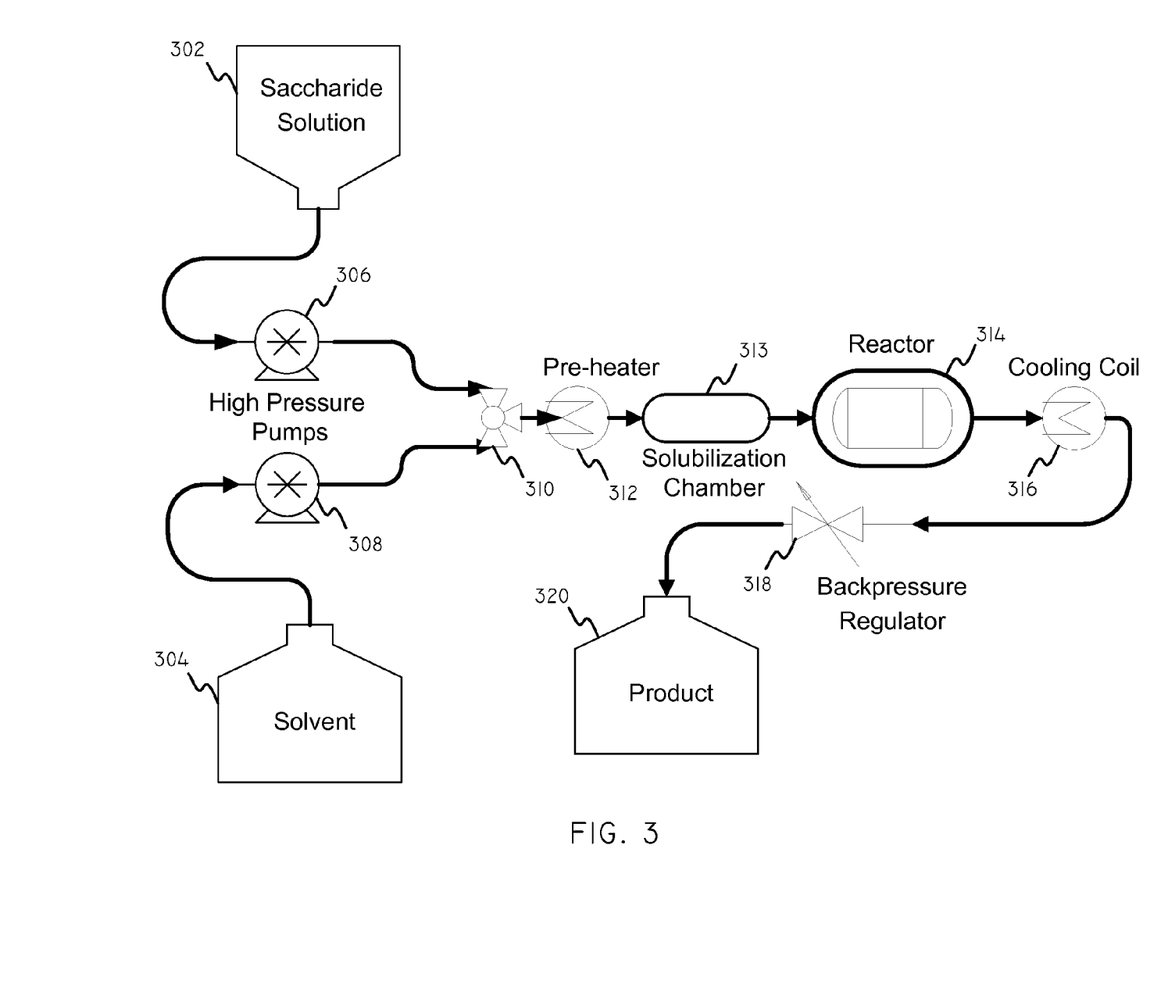
FIG. 3 is a schematic diagram of the system setup in example 2 below.

A reactor system was set up. FIG. 3 shows a schematic view of the reactor system. Two high pressure Waters 590 HPLC pumps 306, 308 (obtained from Waters Corporation, Milford, Mass.) were set up to draw from separate reactant reservoirs (for example, a saccharide solution reservoir 302 and an organic solvent reservoir 304) that were continuously sparged with nitrogen to minimize the effect of dissolved oxygen on the system. The connecting tubing in the system consisted of standard 1/16" stainless steel HPLC tubing (Altech Associates, Deerfield, Ill.).

The reactant solution streams were combined using a "T" 310 and then passed through an electrically driven preheater 312 that was capable of bringing the mixture to the desired set point temperature before entering the independently thermostated fixed bed catalytic reactor 314 (such as reactor column from example 1). Temperature control was achieved using EZ-Zone PM Watlow (St. Louis, Mo.) temperature controllers. The custom preheater was used to bring the temperature of the flowing fluid up to the desired temperature before it entered the reactor, which consisted of wound stainless steel HPLC tubing in a grooved aluminum cylindrical block with an 800 watt Watlow heater in the center of the cylinder. The backpressure of the system was maintained through the use of a Tescom 6000 backpressure regulator 318 obtained from Tescom (Elk River, Minn.). The product produced then flowed into a product vessel 320. Optionally, a cooling coil 316 could be included with the reactor system. In some embodiments, a solubilization chamber 313 was included in order to solubilize sample material, such as cellulose (see examples 15 and 16 below). The use of such a chamber can facilitate implementation as a continuous flow process.

Unless otherwise stated, the percent conversion of saccharide solutions to HMF was determined by high performance liquid chromatography (HPLC). Samples were diluted in HPLC-grade water from both product layers (organic and aqueous). The samples were analyzed isocratically using a mobile phase that consisted of 90% 10 mM $NH_4H_2PO_4$ in $H_2O$ and 10% acetonitrile and a column temperature of 60° C. on an Agilent 1100 using a ZirChrom®-CARB column (50 mm×4.6 mm i.d., 3 µm) (ZirChrom Separations, Inc., Anoka, Minn.) at a mobile phase flow rate of 1 mL/min and using UV detection at 254 nm. A single-point calibration was used for analysis using a fresh standard solution of HMF (Sigma-Aldrich, St. Louis, Mo.) was prepared in HPLC-grade water. Selected samples were also analyzed by $^1$H NMR spectroscopy (Varian 300 MHz) in $CDCl_3$ or $D_2O$.

Example 3

Synthesis of HMF from Sucrose

A 50/50 (vol/vol) methanol/water mixture was prepared and then pumped through a reactor set up as described in Example 2 above using a column packed as described in Example 1 above. The column had dimensions of 4.6 mm (inside diameter) by 150 mm in length. The column was packed with titania particles (5 µm average particle diameter, 300 Å average pore diameter). The methanol/water mixture was pumped through the reactor at 1.0 mL/min while the preheater and column were set to 250° C.

Once the desired temperatures were reached a solution including 40 g sucrose, 80 g water, and 180 g methanol was pumped through the reactor at flow rates of 3, 1.8, and 1.2 mL/min. Fractions were collected for each flow rate. Backpressure stayed steady at these contact times. The reactor was cooled down while flushing water/methanol through the column. Analysis by $^1$H NMR verified the presence of 5-HMF as a major decomposition product.

Example 4

Synthesis of HMF from Sucrose

A 50/50 (vol/vol) ethanol/water mixture was prepared and then pumped through a reactor set up as described in Example 2 above using a column packed as described in Example 1 above. The column had dimensions of 4.6 mm (inside diameter) by 150 mm in length. The column was packed with titania particles (5 µm, 300 Å). The ethanol/water mixture was pumped through the reactor at 1.0 mL/min while the preheater and column were set to 280° C.

Once the desired temperatures were reached a solution including 60 g sucrose, 120 g water, and 270 g EtOH was pumped through the reactor at flow rates of 7, 6, and 5 mL/min. Two fractions were collected for each flow rate at 4-5 intervals. Backpressure stayed steady at these contact times. The reactor was cooled down while flushing water/ethanol through the column. Analysis by $^1$H NMR verified the presence of 5-HMF as a major decomposition product.

Example 5

Synthesis of HMF from Sucrose—Biphasic System

Butanol and water were pumped through a reactor set up as described in Example 2 above using a column packed as described in Example 1 above. The column had dimensions of 10.0 mm (inside diameter) by 150 mm in length. The column was packed with titania particles (80 µm, 60 Å). A 50/50 (vol/vol) butanol/water mixture was pumped through the reactor at 1.0 mL/min (0.5 mL/min butanol and 0.5 mL/min water) while the preheater and column were set to 180° C.

A first solution was prepared consisting of 60 g sucrose in 200 mL water (HPLC grade) (solution "A"). A second solution was 1-butanol (solution "B"). The 1-butanol was used to establish a second phase.

Once the desired temperatures were reached solutions A and B were pumped through the reactor at flow rates of 1.0/1.0, 1.0/1.4, 0.6/1.8 and 1.8/0.6 mL/min (A/B), respectively. Contact time was estimated to be 3.3 minutes. Fractions were collected at various times for 7 or 9 minutes. The reactor was cooled down while flushing water and butanol through the column. Experimental parameters are provided in Table 1 below.

TABLE 1

| Experiment # | Alcohol | Sugar Solution | Flow Rate (mL/min) Alcohol | Sugar | Temperature (C.) Column | Preheater | Outlet | Time (min) |
|---|---|---|---|---|---|---|---|---|
| 1 | 1-BuOH | 0.30 g/mL | 1 | 1 | 180 | 180 | 161 | 7 |
| 2 | 1-BuOH | 0.30 g/mL | 1.4 | 1 | 180 | 180 | 163 | 9 |
| 3 | 1-BuOH | 0.30 g/mL | 1.8 | 0.6 | 180 | 180 | 163 | 7 |
| 4 | 1-BuOH | 0.30 g/mL | 1.8 | 0.6 | 180 | 180 | 166 | 9 |
| 5 | 1-BuOH | 0.30 g/mL | 0.6 | 1.8 | 181 | 179 | 159 | 7 |
| 6 | 1-BuOH | 0.30 g/mL | 0.6 | 1.8 | 180 | 180 | 161 | 9 |

Samples were analyzed by HPLC using UV detection at 254 nm. The following HPLC conditions were utilized: Mobile phase: 90/10 10 mM $NH_4H_2PO_4$/ACN; Column: ZirChrom-CARB column 50 mm×4.6 mm, 3 μm, (S/N: CARB103102O); T=40° C.; Flow=1 mL/min, UV=254 nm. A standard solution of 5-HMF in water (~0.50 mg/mL) was prepared prior to analysis. A calibration curve was prepared by injecting different volumes of the standard.

Based on the HPLC analysis, for experiment 2, the yield in the butanol fraction was approximately 10.81 percent and the yield in the water fraction was approximately 4.02 percent. For experiment 4, the yield in the butanol fraction was approximately 10.64 percent and the yield in the water fraction was approximately 2.60 percent. For experiment 6, the yield in the butanol fraction was approximately 3.43 percent and the yield in the water fraction was approximately 19.32 percent.

Example 6

Synthesis of HMF from Sucrose—Biphasic System

Butanol and water were pumped through a reactor set up as described in Example 2 above using a column packed as described in Example 1 above. The column had dimensions of 10.0 mm (inside diameter) by 150 mm in length. The column was packed with titania particles (80 μm, 60 Å). A 50/50 (vol/vol) butanol/water mixture was pumped through the reactor at 1 mL/min (0.5 mL/min butanol and 0.5 mL/min water) while the preheater and column were set to 200° C.

A first solution was prepared consisting of 60 g sucrose in 200 mL water (HPLC grade) (solution "A"). A second solution was 1-butanol (solution "B"). The 1-butanol was used to establish a second phase.

Once the desired temperatures were reached solutions A and B were pumped through the reactor at flow rates of 1.8/0.6, 1.2/1.2, and 0.6/1.8 mL/min, respectively. Contact time was estimated to be 3.3 minutes. Fractions were collected in 9 minute intervals. The reactor was cooled down while flushing water and butanol through the column. Experimental parameters are provided in Table 2 below.

Mobile phase: 90/10 10 mM $NH_4H_2PO_4$/ACN; Column: ZirChrom-CARB column 50 mm×4.6 mm, 3 μm, (S/N: CARB103102O); T=40° C.; Flow=1 mL/min, UV=254 nm. A standard solution of 5-HMF in water (~0.50 mg/mL) was prepared prior to analysis. A calibration curve was prepared by injecting different volumes of the standard.

Based on the HPLC analysis, for experiment 2, the yield in the butanol fraction was approximately 4.55 percent and the yield in the water fraction was approximately 9.35 percent. For experiment 4, the yield in the butanol fraction was approximately 7.67 percent and the yield in the water fraction was approximately 5.86 percent. For experiment 6, the yield in the butanol fraction was approximately 10.81 percent and the yield in the water fraction was approximately 2.68 percent.

Example 7

Synthesis of HMF from Glucose—Biphasic System

Butanol and water were pumped through a reactor set up as described in Example 2 above using a column packed as described in Example 1 above. The column had dimensions of 10.0 mm (inside diameter) by 150 mm in length. The column was packed with titania particles (80 μm, 60 Å). A 50/50 (vol/vol) butanol and water mixture was pumped through the reactor at 1 mL/min (0.5 mL/min butanol and 0.5 mL/min water) while the preheater and column were set to 180° C.

A first solution was prepared consisting of 60 g glucose in 200 mL water (HPLC grade) (solution "A"). A second solution was 1-butanol (solution "B"). The 1-butanol was used to establish a second phase.

Once the desired temperatures were reached solutions A and B were pumped through the reactor at flow rates of 1.8/0.6, 1.2/1.2, and 0.6/1.8 mL/min, respectively. Contact time was estimated to be 3.3 minutes. Fractions were collected in 9 minute intervals. The reactor was cooled down while flushing water and butanol through the column. Experimental parameters are provided in Table 3 below.

TABLE 2

| Experiment # | Alcohol | Sugar Solution | Flow Rate (mL/min) | | Temperature (C.) | | | Time (min) |
|---|---|---|---|---|---|---|---|---|
| | | | Alcohol | Sugar | Column | Preheater | Outlet | |
| 1 | 1-BuOH | 0.30 g/mL | 0.6 | 1.8 | 200 | 200 | 200 | 9 |
| 2 | 1-BuOH | 0.30 g/mL | 0.6 | 1.8 | 200 | 200 | 201 | 9 |
| 3 | 1-BuOH | 0.30 g/mL | 1.2 | 1.2 | 199 | 200 | 204 | 9 |
| 4 | 1-BuOH | 0.30 g/mL | 1.2 | 1.2 | 200 | 200 | 203 | 9 |
| 5 | 1-BuOH | 0.30 g/mL | 1.8 | 0.6 | 200 | 200 | 202 | 9 |
| 6 | 1-BuOH | 0.30 g/mL | 1.8 | 0.6 | 200 | 200 | 203 | 9 |

Samples were analyzed by HPLC using UV detection at 254 nm. The following HPLC conditions were utilized:

TABLE 3

| Experiment # | Alcohol | Sugar Solution | Flow Rate (mL/min) | | Temperature (C.) | | | Time (min) |
|---|---|---|---|---|---|---|---|---|
| | | | Alcohol | Sugar | Column | Preheater | Outlet | |
| 1 | 1-BuOH | 0.30 g/mL | 0.6 | 1.8 | 180 | 180 | 184 | 9 |
| 2 | 1-BuOH | 0.30 g/mL | 1.2 | 1.2 | 180 | 180 | 184 | 10 |
| 3 | 1-BuOH | 0.30 g/mL | 1.2 | 1.2 | 180 | 180 | 184 | 9 |

TABLE 3-continued

| Experiment # | Alcohol | Sugar Solution | Flow Rate (mL/min) | | Temperature (C.) | | | Time (min) |
|---|---|---|---|---|---|---|---|---|
| | | | Alcohol | Sugar | Column | Preheater | Outlet | |
| 4 | 1-BuOH | 0.30 g/mL | 1.8 | 0.6 | 180 | 180 | 184 | 12 |
| 5 | 1-BuOH | 0.30 g/mL | 1.8 | 0.6 | 180 | 180 | 183 | 9 |

Samples were analyzed by HPLC using UV detection at 254 nm. The following HPLC conditions were utilized: Mobile phase: 90/10 10 mM $NH_4H_2PO_4$/ACN; Column: ZirChrom-CARB column 50 mm×4.6 mm, 3 μm, (S/N: CARB103102O); T=40° C.; Flow=1 mL/min, UV=254 nm. A standard solution of 5-HMF in water (~0.50 mg/mL) was prepared prior to analysis. A calibration curve was prepared by injecting different volumes of the standard.

Based on the HPLC analysis, for experiment 1, the yield in the butanol fraction was approximately 2.23 percent and the yield in the water fraction was approximately 3.94 percent. For experiment 3, the yield in the butanol fraction was approximately 5.51 percent and the yield in the water fraction was approximately 3.09 percent. For experiment 5, the yield in the butanol fraction was approximately 11.64 percent and the yield in the water fraction was approximately 2.47 percent.

Example 8

Synthesis of HMF from Glucose—Biphasic System

Butanol and water were pumped through a reactor set up as described in Example 2 above using a column packed as described in Example 1 above. The column had dimensions of 10.0 mm (inside diameter) by 150 mm in length. The column was packed with titania particles (80 μm, 60 Å). A 50/50 (vol/vol) butanol and water mixture was pumped through the reactor at 1 mL/min (0.5 mL/min butanol and 0.5 mL/min water) while the preheater and column were set to 200° C.

A first solution was prepared consisting of 60 g glucose in 200 mL water (HPLC grade) (solution "A"). A second solution was 1-butanol (solution "B"). The 1-butanol was used to establish a second phase.

Once the desired temperatures were reached solutions A and B were pumped through the reactor at flow rates of 1.8/0.6, 1.2/1.2, and 0.6/1.8 mL/min, respectively. Contact time was estimated to be 3.3 minutes. Fractions were collected in 9 minute intervals. Reactor was cooled down while flushing water and butanol through the column. Experimental parameters are provided in Table 4 below.

Samples were analyzed by HPLC using UV detection at 254 nm. The following HPLC conditions were utilized: Mobile phase: 90/10 10 mM $NH_4H_2PO_4$/ACN; Column: ZirChrom-CARB column 50 mm×4.6 mm, 3 μm, (S/N: CARB103102O); T=40° C.; Flow=1 mL/min, UV=254 nm. A standard solution of 5-HMF in water (~0.50 mg/mL) was prepared prior to analysis. A calibration curve was prepared by injecting different volumes of the standard.

Based on HPLC analysis, for experiment 1, the yield in the butanol fraction was approximately 4.60 percent and the yield in the water fraction was approximately 8.49 percent. For experiment 3, the yield in the butanol fraction was approximately 8.37 percent and the yield in the water fraction was approximately 5.36 percent. For experiment 5, the yield in the butanol fraction was approximately 5.40 percent and the yield in the water fraction was approximately 7.14 percent.

Example 9

Synthesis of HMF from Fructose—Biphasic System

Butanol and water were pumped through a reactor set up as described in Example 2 above using a column packed as described in Example 1 above. The column had dimensions of 10.0 mm (inside diameter) by 150 mm in length. The column was packed with titania particles (80 μm, 60 Å). A 50/50 butanol and water mixture was pumped through the reactor at 1 mL/min (0.5 mL/min butanol and 0.5 mL/min water) while the preheater and column were set to 180° C.

A first solution was prepared consisting of 60 g fructose in 200 mL water (HPLC grade) (solution "A"). A second solution was 1-butanol (solution "B"). The 1-butanol was used to establish a second phase.

Once the desired temperatures were reached solutions A and B were pumped through the reactor at flow rates of 1.8/0.6, 1.2/1.2, and 0.6/1.8 mL/min, respectively. Contact time was estimated to be 3.3 minutes. Fractions were collected in 9 minute intervals. The reactor was then heated to 200° C. Solutions A and B were pumped through the reactor at flow rates of 1.8/0.6, 1.2/1.2, and 0.6/1.8 mL/min, respectively. Fractions were collected in 9 minute intervals. The reactor was cooled down while flushing water and butanol through the column. Experimental parameters are provided in Table 5 below.

TABLE 4

| Experiment # | Alcohol | Sugar Solution | Flow Rate (mL/min) | | Temperature (C.) | | | Time (min) |
|---|---|---|---|---|---|---|---|---|
| | | | Alcohol | Sugar | Column | Preheater | Outlet | |
| 1 | 1-BuOH | 0.30 g/mL | 0.6 | 1.8 | 200 | 200 | 206 | 10 |
| 2 | 1-BuOH | 0.30 g/mL | 1.2 | 1.2 | 200 | 200 | 205 | 10 |
| 3 | 1-BuOH | 0.30 g/mL | 1.2 | 1.2 | 200 | 200 | 205 | 10 |
| 4 | 1-BuOH | 0.30 g/mL | 1.8 | 0.6 | 200 | 200 | 204 | 15 |
| 5 | 1-BuOH | 0.30 g/mL | 1.8 | 0.6 | 200 | 200 | 204 | 10 |

TABLE 5

| Experiment # | Alcohol | Sugar Solution | Flow Rate (mL/min) | | Temperature (C.) | | | Time (min) |
|---|---|---|---|---|---|---|---|---|
| | | | Alcohol | Sugar | Column | Preheater | Outlet | |
| 1 | 1-BuOH | 0.30 g/mL | 0.6 | 1.8 | 180 | 180 | 185 | 9 |
| 2 | 1-BuOH | 0.30 g/mL | 1.2 | 1.2 | 180 | 180 | 184 | 10 |
| 3 | 1-BuOH | 0.30 g/mL | 1.2 | 1.2 | 180 | 180 | 184 | 9 |
| 4 | 1-BuOH | 0.30 g/mL | 1.8 | 0.6 | 180 | 180 | 184 | 9 |
| 5 | 1-BuOH | 0.30 g/mL | 1.8 | 0.6 | 180 | 180 | 184 | 9 |
| 6 | 1-BuOH | 0.30 g/mL | 0.6 | 1.8 | 200 | 200 | 204 | 14 |
| 7 | 1-BuOH | 0.30 g/mL | 0.6 | 1.8 | 200 | 200 | 203 | 9 |
| 8 | 1-BuOH | 0.30 g/mL | 1.2 | 1.2 | 200 | 200 | 203 | 9 |
| 9 | 1-BuOH | 0.30 g/mL | 1.2 | 1.2 | 200 | 200 | 203 | 11 |
| 10 | 1-BuOH | 0.30 g/mL | 1.8 | 0.6 | 200 | 200 | 203 | 9 |
| 11 | 1-BuOH | 0.30 g/mL | 1.8 | 0.6 | 200 | 200 | 203 | 10 |

Samples were analyzed by HPLC using UV detection at 254 nm. The following HPLC conditions were utilized: Mobile phase: 90/10 10 mM $NH_4H_2PO_4$/ACN; Column: ZirChrom-CARB column 50 mm×4.6 mm, 3 μm, (S/N: CARB103102O); T=40° C.; Flow=1 mL/min, UV=254 nm. A standard solution of 5-HMF in water (~0.50 mg/mL) was prepared prior to analysis. A calibration curve was prepared by injecting different volumes of the standard.

Based on HPLC analysis, for experiment 1, the yield in the butanol fraction was approximately 2.94 percent and the yield in the water fraction was approximately 8.73 percent. For experiment 3, the yield in the butanol fraction was approximately 5.16 percent and the yield in the water fraction was approximately 3.09 percent. For experiment 5, the yield in the butanol fraction was approximately 9.17 percent and the yield in the water fraction was approximately 1.94 percent. For experiment 7, the yield in the butanol fraction was approximately 6.41 percent and the yield in the water fraction was approximately 12.96 percent. For experiment 9, the yield in the butanol fraction was approximately 9.02 percent and the yield in the water fraction was approximately 5.70 percent. For experiment 11, the yield in the butanol fraction was approximately 11.19 percent and the yield in the water fraction was approximately 2.62 percent.

Example 10

Synthesis of HMF from Fructose—Biphasic System

Butanol and water were pumped through a reactor set up as described in Example 2 above using a column packed as described in Example 1 above. The column had dimensions of 10.0 mm (inside diameter) by 150 mm in length. The column was packed with titania particles (80 μm, 60 Å). A 50/50 butanol and water mixture was pumped through the reactor at 1 mL/min (0.5 mL/min butanol and 0.5 mL/min water) while the preheater and column were set to 200° C.

A first solution was prepared consisting of 60 g fructose in 200 mL water (HPLC grade) (solution "A"). A second solution was 1-butanol (solution "B"). The 1-butanol was used to establish a second phase.

Once the desired temperatures were reached solutions A and B were pumped through the reactor at flow rates of 1.2/0.4, 1.0/0.6, 0.8/0.8, 0.6/1.0, and 0.4/1.2 mL/min, respectively. Contact time was estimated to be 5 minutes. Fractions were collected in various time intervals. The reactor was cooled down while flushing water and butanol through the column. Experimental parameters are provided in Table 6 below.

TABLE 6

| Experiment # | Alcohol | Sugar Solution | Flow Rate (mL/min) | | Temperature (C.) | | | Time (min) |
|---|---|---|---|---|---|---|---|---|
| | | | Alcohol | Sugar | Column | Preheater | Outlet | |
| 1 | 1-BuOH | 0.30 g/mL | 0.4 | 1.2 | 200 | 200 | 208 | 10 |
| 2 | 1-BuOH | 0.30 g/mL | 0.4 | 1.2 | 200 | 200 | 206 | 16 |
| 3 | 1-BuOH | 0.30 g/mL | 0.4 | 1.2 | 200 | 200 | 206 | 10 |
| 4 | 1-BuOH | 0.30 g/mL | 0.6 | 1 | 200 | 200 | 206 | 11 |
| 5 | 1-BuOH | 0.30 g/mL | 0.6 | 1 | 200 | 200 | 206 | 10 |
| 6 | 1-BuOH | 0.30 g/mL | 0.8 | 0.8 | 200 | 200 | 206 | 12 |
| 7 | 1-BuOH | 0.30 g/mL | 0.8 | 0.8 | 200 | 200 | 206 | 10 |
| 8 | 1-BuOH | 0.30 g/mL | 1 | 0.6 | 200 | 200 | 206 | 13 |
| 9 | 1-BuOH | 0.30 g/mL | 1 | 0.6 | 200 | 200 | 206 | 8 |
| 10 | 1-BuOH | 0.30 g/mL | 1.2 | 0.4 | 200 | 200 | 206 | 12 |
| 11 | 1-BuOH | 0.30 g/mL | 1.2 | 0.4 | 200 | 200 | 206 | 10 |

Samples were analyzed by HPLC using UV detection at 254 nm. The following HPLC conditions were utilized: Mobile phase: 90/10 10 mM $NH_4H_2PO_4$/ACN; Column: ZirChrom-CARB column 50 mm×4.6 mm, 3 μm, (S/N: CARB103102O); T=40° C.; Flow=1 mL/min, UV=254 nm. A standard solution of 5-HMF in water (~0.50 mg/mL) was prepared prior to analysis. A calibration curve was prepared by injecting different volumes of the standard.

Based on HPLC analysis, for experiment 3, the yield in the butanol fraction was approximately 0.84 percent and the yield in the water fraction was approximately 17.59 percent. For experiment 5, the yield in the butanol fraction was approximately 11.27 percent and the yield in the water fraction was approximately 11.16 percent. For experiment 7, the yield in the butanol fraction was approximately 11.64 percent and the yield in the water fraction was approximately 7.54 percent. For experiment 9, the yield in the butanol fraction was approximately 7.14 percent and the yield in the water fraction was approximately 2.45 percent. For experiment 11, the yield in the butanol fraction was approximately 9.40 percent and the yield in the water fraction was approximately 2.02 percent.

Example 11

Synthesis of HMF from Sucrose—Monophasic System

Various alcohols (isopropyl alcohol—IPA, ethanol—EtOH, or methanol—MeOH) and various temperatures were tested in regard to conversion of sucrose to HMF. Both zirconia and titania were used as catalysts. The zirconia (zirconium dioxide) consisted of particles with a diameter of 25 μm and average pore size of 300 Å. The titania consisted of particles with a diameter of 80 μm and average pore size of 60 Å. The conditions and results are shown below in TABLE 7.

TABLE 7

| Solution | Temp (° C.) | Contact Time (min) | Back Pressure (psi) | % HMF | Catalyst |
|---|---|---|---|---|---|
| 4 g sucrose/10 g H2O/28 g IPA | 180 | 2 | 1000 | 11 | ZrO2 |
| 10 g sucrose/20 g H2O/50 g IPA | 180 | 2 | 1000 | 12 | TiO2 |
| 60 g sucrose/120 g H2O/270 g EtOH | 280 | 1 | 1500 | 10 | TiO2 |
| 40 g sucrose/80 g H2O/180 g MeOH | 250 | 5 | 1500 | 13 | TiO2 |
| 20 g sucrose/40 g H2O/180 g MeOH | 270 | 5 | 1500 | 14 | TiO2 |

Example 12

Synthesis of HMF from Glucose with Homogenous Acid Co-Catalyst

The effects of a homogenous acid co-catalyst (hydrochloric acid or phosphoric acid) were tested on the efficiency of conversion of glucose (50% w/w glucose solution in water) to HMF. Titania particles with a diameter of 80 μm and average pore size of 60 Å were used as the other catalyst. Methyl isobutyl ketone (MIBK) was used as the organic solvent. Samples were otherwise run using a system substantially as described in Example 2 above. The conditions and results are shown in Table 8 below.

TABLE 8

| Organic Solvent | Temp (° C.) | Org:Aq ratio | Back pressure(psi) | % HMF | Contact time (min) | Catalyst | Co-catalyst |
|---|---|---|---|---|---|---|---|
| MIBK | 180 | 10:1 | 1000 | 13 | 2 | None | 0.15 M HCl |
| MIBK | 180 | 10:1 | 1000 | 46 | 2 | TiO2 | 0.15 M HCl |
| MIBK | 180 | 10:1 | 1000 | 42 | 2 | TiO2 | 0.10 M HCl |
| MIBK | 180 | 10:1 | 1000 | 29 | 2 | TiO2 | 0.05 M HCl |
| MIBK | 180 | 10:1 | 1000 | 33 | 2 | TiO2 | 0.10 M H3PO4 |

Example 13

Synthesis of HMF from Glucose with Phosphate Modified Zirconia

The zirconia catalyst was modified using phosphoric acid. Specifically, a solution of 0.1 M $H_3PO_4$ was passed through a catalytic reactor packed with 25 μm zirconia particles for 20 column volumes (~160 mL). The reactor was then washed with HPLC grade water for 10 column volumes (~80 mL). The phosphate modified catalytic reactor was then tested for activity in the conversion of glucose (33% w/w glucose solution in water) to HMF. Samples were otherwise run using a system as described in Example 2 above. The organic solvents used included methyl isobutyl ketone (MIBK), or mixtures of MIBK with 2-butanol (2-BuOH) and 4-methyl-2-pentanol (4M2P). Decreased yields were observed as compared to the unmodified zirconia catalyst as shown in Table 9 below.

TABLE 9

| Organic Solvent | Temp (° C.) | Org:Aq ratio | Back pressure (psi) | % HMF | Contact time (min) | Catalyst |
|---|---|---|---|---|---|---|
| MIBK | 180 | 10:1 | 500 | 15 | 2 | ZrO2 |
| 7:3 MIBK/2-BuOH | 160 | 10:1 | 500 | 8 | 2 | ZrO2 |
| 7:3 MIBK/2-BuOH | 160 | 10:1 | 500 | 8 | 2 | ZrO2 |
| 7:3 MIBK/4M2P | 180 | 10:1 | 500 | 7 | 2 | ZrO2 |

Example 14

Synthesis of HMF from Glucose with Regenerated Titania Catalyst

Titania particles with a diameter of 80 μm and average pore size of 60 Å were obtained after displayed diminished catalytic activity or otherwise were part of the reactor that had plugged to the point that liquid could not be pumped through the system. The titania particles were recovered by unpacking the reactor and allowed to air dry. The dried material was transferred to a sintering oven and heated to 450 C for 5 hours or until the catalyst was a light tank color again. The regenerated catalyst was then packed in a new reactor and tested for active by the conversion of glucose to HMF. The conditions and results are show below in Table 10.

TABLE 10

| Organic Solvent | Temp (° C.) | Org:Aq ratio | Back pressure(psi) | % HMF | Contact time (min) | Regeneration |
|---|---|---|---|---|---|---|
| MIBK | 180 | 10:1 | 1000 | 26 | 2 | 0 |
| MIBK | 180 | 10:1 | 1000 | 30 | 2 | 1st |
| MIBK | 180 | 10:1 | 1000 | 27 | 2 | 2nd |

Example 15

Synthesis of Biofuel from Glucose and Cellulose

A system was set up similar to that described in Example 2. However, the system included two catalytic reactors. Both reactors were packed with titania particles (80 μm and average pore size of 60 Å). One reactor was 250 mm×10 mm and the other reactor was 150 mm×10 mm.

A 50% (w/w) glucose solution and denatured ethanol were pumped through the reactor system at 0.43 and 13.78 mL/min, respectively, giving a catalyst contact time of 90 s. The preheater was set to 320° C. and the column heater set to 370° C. The back pressure was set at 2000 psi and the experiment was conducted over 5 hours. The reactor was cooled by flushing the system with 100% denatured ethanol.

The collected biofuel solution was then concentrated by rotary evaporation to yield a transparent brown, sweet-smelling liquid. A 5 hour experiment yielded ~50 g of biofuel. The biofuel was then submitted for selected ASTM fuel testing. The results are shown in Table 11 below.

TABLE 11

| ASTM Test | Result |
|---|---|
| ASTM D1298 - API Gravity - FO | 19 |
| AF-3 - Sulfate Ash | N/A |
| ASTM D4530 - Carbon Residue | 1.80% |
| ASTM D976 - Cetane Index | 20.61 |
| ASTM D2500 - Cloud Point | −41.5° C. |
| ASTM D130 - Copper Strip Corrosion Rating | 2 |
| ASTM D86 - Distillation, % Recovery | N/A |
| ASTM D86 - Distillation, 10% Recovery | 192° C. |
| ASTM D86 - Distillation, 50% Recovery | 248° C. |
| ASTM D86 - Distillation, 90% Recovery | 306° C. |
| ASTM D86 - Distillation, End Point | 271° C. |
| ASTM D86 - Distillation, IBP | 143° C. |
| ASTM D93 - Flashpoint, PMCC | 50.5° C. |
| Du Pont F21-61 - Stability & Accelerated Aging | 1.91-3.08 |
| ASTM D445 - Viscosity @40 C. | 4.26 mm$^2$/s |

Next, 4.6 g microcrystalline cellulose was packed into a 150 mm×10 mm cylindrical steel tube, with 40 mm frits and end fittings for connecting to HPLC tubing added. This apparatus (or solubilizing chamber) was placed in between the preheater and the catalytic reactor. A solution of denatured ethanol was pumped through the system at 4 mL/min giving a catalyst contact time of 2 min. The preheater was set to 350° C., the column heater was set to 350° C. and the back pressure was set to 2000 psi. After 1 hour the system was rapidly cooled by removal from the heater and immersion in water. The remaining contents of the solubilizing chamber were collected using a Buchner funnel and the material carefully dried and weighed. 0.25 g of unreacted cellulose recovered corresponding to a 94% conversion.

The collected biofuel solution was then concentrated by rotary evaporation to yield a transparent brown, sweet-smelling liquid. The 1 hour experiment yielded ~4 g of biofuel.

Figure 4:
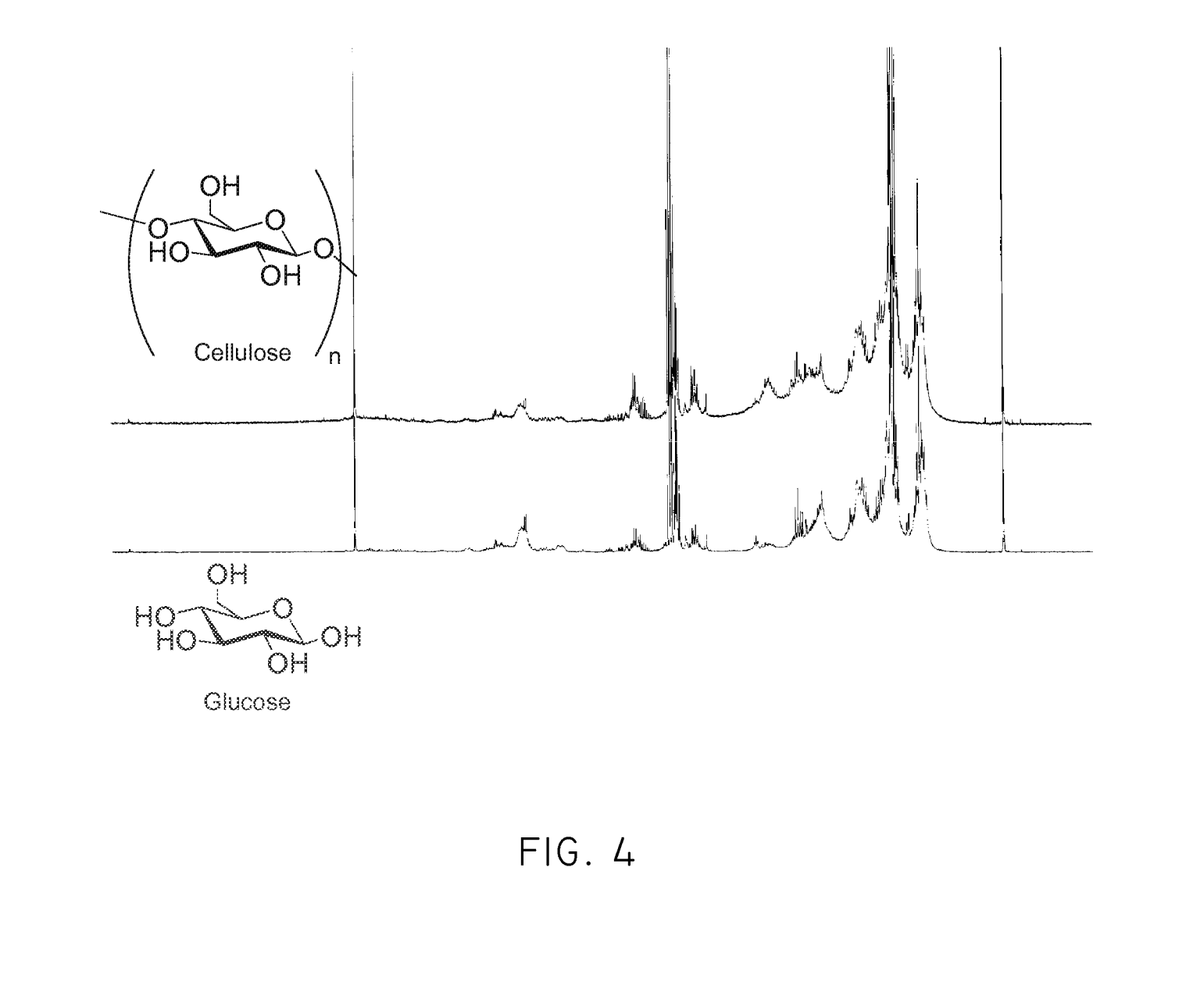
FIG. 4 is a comparative $^1$H-NMR (300 MHz, CDCl$_3$) spectra for the biofuels obtained in example 15 below.

FIG. 4 is a comparative $^1$H-NMR (300 MHz, CDCl$_3$) for the biofuels obtained from cellulose and glucose. This shows that cellulose can be turned into biofuel in accordance with embodiments herein.

Example 16

Synthesis of HMF from Various Substrates with Varied Conditions

Using a system substantially as described with reference to example 2 above, inputs and conditions were varied in order to determine the effect on HMF synthesis. The conversions of glucose, fructose and sucrose were investigated using a porous titania catalyst and n-butanol as the extracting solvent (Table 12, runs 1-16). The ratio of extracting solvent to aqueous solution was varied for each sugar substrate and reactor temperatures were ranged from 180 to 200° C. Yields were found to be higher at lower organic/aqueous ratios except in the case of glucose. While not intending to be bound by theory, it is viewed as being possible that under the conditions studied the system is not truly biphasic. In this regard, monophasic reactions with methanol and ethanol gave similar yields to those observed for n-butanol, suggesting that the reaction may actually be one phase in the reactor, nullifying the ability of the n-butanol to act as an extracting solvent. However, the possibility that the alcohol is interacting with the catalyst surface preferentially cannot be excluded. Fructose was then selected for a brief investigation of the effect of contact time which was varied from 3 to 5 minutes (Table 12, runs 19-21). Interestingly, there was little effect on the yield of HMF observed at longer contact times with the catalyst. In fact, as the catalyst contact times are increased, some humic material was observed in the resulting product solution. This can eventually lead to plugging of the reactor system.

Due to the relatively poor performance of n-butanol, alternative extracting solvents were considered. In particular, methyl isobutyl ketone (MIBK) was studied. Employing MIBK as an extracting solvent led to increased HMF yields (Table 12, runs 23-24). The use of an alcohol co-solvent with MIBK was also investigated. Surprisingly, a 7:3 mixture of MIBK and 2-butanol gave a decreased yield of HMF in our system (Table 12, run 26). The co-solvent 4-methyl-2-butanol was also tried. This solvent was selected because of its decreased water solubility and its structural similarity to MIBK. A ratio of MIBK to 4-methyl-2-butanol of 9:1 was used and a decrease in yield was observed, suggesting that the alcohol has some deleterious effect on the reaction (Table 12, run 28). Further studies were conducted with just MIBK. A 2% yield of HMF was obtained when no catalyst was present (Table 12, run 31) in the reactor as compared to a 30% yield of HMF with titania catalyst used under identical, optimized conditions (Table 12, run 32).

The use of a homogenous acid co-catalyst was also briefly investigated. When the sugar solution was prepared in 0.15 M HCl the yield of HMF was increased to 46% in the presence of both catalysts (Table 1, run 30). Under the same reaction conditions with no metal oxide catalyst a 13% yield of HMF was obtained (Table 1, run 29). It will be noted that runs 29 and 30 correspond to example 12 above. The substrate for runs 29 and 30 was prepared in 0.15 M hydrochloric acid.

In order to study the possibility of using the catalytic system for the conversion of polysaccharides to HMF, the use of common oligosaccharide sources, including corn syrup which was diluted to a 60% (w/w) aqueous sugar solution (Table 1, runs 33-37) was investigated. The results were surprising as the observed HMF yields were higher than those observed for monosachharide solutions, namely 41% versus 30%, respectively. While not intending to be bound by theory, it is believed that the yield increase may be attributed to the salt present in the corn syrup through the well known hydrophobic salting out effect. A 5% solution of water-soluble starch was prepared for conversion to HMF. This polysaccharide source is comprised of shorter chain starch polymers and using optimized conditions was converted to HMF with a 29% yield (Table 1, run 37). The results are summarized in table 12.

cellulose enters the catalytic reactor and is first hydrolyzed, and then subsequently converted to HMF. In this fashion a continuous conversion of cellulose to HMF was achieved as shown in Table 13. The effect of solution temperature on yield of HMF was systematically studied from 260 to 280° C. At a reaction temperature of 260° C., 67% of the cellulose was converted to HMF with a 37% yield (Table 2, run 38). A 10 degree increase resulted in an average cellulose conversion of 87% and HMF yield of 48% (Table 2, run 39-40). At 280° C.

TABLE 12

| Run | Substrate | Concentration (w/w) | Organic Solvent | Temp (° C.) | Org:Aq ratio | Back pressure (psi) | % HMF | Contact Time (min) | Catalyst |
|---|---|---|---|---|---|---|---|---|---|
| 1 | Glucose | 23% | n-BuOH | 180 | 1:3 | 2000 | 6 | 3 | $TiO_2$ |
| 2 | Glucose | 23% | n-BuOH | 180 | 1:1 | 2000 | 8 | 3 | $TiO_2$ |
| 3 | Glucose | 23% | n-BuOH | 180 | 3:1 | 2000 | 14 | 3 | $TiO_2$ |
| 4 | Glucose | 23% | n-BuOH | 200 | 1:3 | 2000 | 13 | 3 | $TiO_2$ |
| 5 | Glucose | 23% | n-BuOH | 200 | 1:1 | 2000 | 13 | 3 | $TiO_2$ |
| 6 | Glucose | 23% | n-BuOH | 200 | 3:1 | 2000 | 12 | 3 | $TiO_2$ |
| 7 | Fructose | 23% | n-BuOH | 180 | 1:3 | 2000 | 11 | 3 | $TiO_2$ |
| 8 | Fructose | 23% | n-BuOH | 180 | 1:1 | 2000 | 8 | 3 | $TiO_2$ |
| 9 | Fructose | 23% | n-BuOH | 180 | 3:1 | 2000 | 12 | 3 | $TiO_2$ |
| 10 | Fructose | 23% | n-BuOH | 200 | 1:3 | 2000 | 18 | 3 | $TiO_2$ |
| 11 | Fructose | 23% | n-BuOH | 200 | 1:1 | 2000 | 14 | 3 | $TiO_2$ |
| 12 | Fructose | 23% | n-BuOH | 200 | 3:1 | 2000 | 13 | 3 | $TiO_2$ |
| 13 | Sucrose | 23% | n-BuOH | 180 | 1:3 | 2000 | 22 | 3 | $TiO_2$ |
| 14 | Sucrose | 23% | n-BuOH | 180 | 1:1 | 2000 | 14 | 3 | $TiO_2$ |
| 15 | Sucrose | 23% | n-BuOH | 180 | 3:1 | 2000 | 13 | 3 | $TiO_2$ |
| 16 | Sucrose | 23% | n-BuOH | 200 | 1:3 | 2000 | 14 | 3 | $TiO_2$ |
| 17 | Sucrose | 23% | n-BuOH | 200 | 1:1 | 2000 | 13 | 3 | $TiO_2$ |
| 18 | Sucrose | 23% | n-BuOH | 200 | 3:1 | 2000 | 13 | 3 | $TiO_2$ |
| | | | Contact Time | | | | | | |
| 19 | Fructose | 23% | n-BuOH | 200 | 3:1 | 2000 | 13 | 3 | $TiO_2$ |
| 20 | Fructose | 23% | n-BuOH | 200 | 1:3 | 2000 | 18 | 3 | $TiO_2$ |
| 21 | Fructose | 23% | n-BuOH | 200 | 3:1 | 2000 | 11 | 5 | $TiO_2$ |
| 22 | Fructose | 23% | n-BuOH | 200 | 1:3 | 2000 | 18 | 5 | $TiO_2$ |
| | | | Catalyst | | | | | | |
| 23 | Glucose | 23% | MIBK | 180 | 10:1 | 500 | 30 | 2 | $TiO_2$ |
| 24 | Glucose | 23% | MIBK | 180 | 10:1 | 500 | 28 | 2 | $ZrO_2$ |
| | | | Solvent Composition | | | | | | |
| 25 | Glucose | 50% | MIBK | 180 | 10:1 | 2000 | 27 | 2 | $TiO_2$ |
| 26 | Glucose | 50% | 7:3 MIBK/2-BuOH | 180 | 10:1 | 2000 | 22 | 2 | $TiO_2$ |
| 27 | Glucose | 50% | MIBK | 180 | 10:1 | 2000 | 26 | 2 | $TiO_2$ |
| 28 | Glucose | 50% | 9:1 MIBK/4M2P | 180 | 10:1 | 2000 | 14 | 2 | $TiO_2$ |
| | | | Co-Catalyst and Blank | | | | | | |
| 29* | Glucose | 50% | MIBK | 180 | 10:1 | 1000 | 13 | 2 | None |
| 30* | Glucose | 50% | MIBK | 180 | 10:1 | 1000 | 46 | 2 | $TiO_2$ |
| 31 | Glucose | 50% | MIBK | 180 | 10:1 | 1000 | 2 | 2 | None |
| 32 | Glucose | 50% | MIBK | 180 | 10:1 | 1000 | 30 | 2 | $TiO_2$ |
| | | | Other Substrates | | | | | | |
| 33 | Lite Corn Sy | 60% | MIBK | 180 | 10:1 | 1000 | 41 | 2 | $TiO_2$ |
| 34 | Lite Corn Sy | 60% | MIBK | 160 | 10:1 | 1000 | 30 | 2 | $TiO_2$ |
| 35 | Honey | 50% | MIBK | 170 | 10:1 | 1000 | 27 | 2 | $TiO_2$ |
| 36 | Glu/Fru/Suc | (20/20/10) 50% | MIBK | 180 | 10:1 | 1000 | 24 | 2 | $TiO_2$ |
| 37 | Starch | 5% | MIBK | 180 | 10:1 | 1000 | 29 | 2 | $TiO_2$ |

Next, the conversion of cellulose to HMF was investigated. In order to conduct this experiment, microcrystalline cellulose obtained from Sigma Chemical (St. Louis, Mo.) was placed into a 150×10 mm "solubilizing" chamber and installed between the preheater and the catalytic reactor. The preheater was used to bring a 5:1 MIBK:$H_2O$ mixture to the desired temperature and the hot mixture was passed through the chamber containing the cellulose. The lower organic to aqueous ratio was chosen because it was believed that the water would provide the medium for solubilizing the cellulose. At elevated temperature and pressure the solubilized cellulose enters the catalytic reactor and is first hydrolyzed, and then subsequently converted to HMF. In this fashion a continuous conversion of cellulose to HMF was achieved as shown in Table 13. The effect of solution temperature on yield of HMF was systematically studied from 260 to 280° C. At a reaction temperature of 260° C., 67% of the cellulose was converted to HMF with a 37% yield (Table 2, run 38). A 10 degree increase resulted in an average cellulose conversion of 87% and HMF yield of 48% (Table 2, run 39-40). At 280° C. severe plugging occurred of the outgoing frits in the cellulose extraction chamber, likely due to charring (Table 13, run 42). A thermal gradient dissolution approach to solubilizing the cellulose was also performed by starting at 260° C. and increasing 10 degrees every 20 minutes until reaching 280° C. A 72% conversion of cellulose was achieved using this approach with a 40% yield of HMF (Table 13, run 42). Remarkably, it was discovered that using this continuous flow reactor system and an ultra-stable porous heterogeneous metal oxide catalyst, cellulose can be converted directly to HMF in good yields and high conversions.

TABLE 13

| Run | Substrate | Cellulose (g) | Organic Solvent | Temp Range (° C.) | Org:Aq Ratio | Back Pressure (psi) | Recovered Cellulose (g) | Conversion | HMF Yield | Time (min) |
|---|---|---|---|---|---|---|---|---|---|---|
| 38 | Cellulose | 5.30 | MIBK | 260 | 5:1 | 1000 | 2.29 | 68% | 37% | 60 |
| 39 | Cellulose | 5.00 | MIBK | 270 | 5:1 | 1000 | 0.31 | 95% | 48% | 60 |
| 40 | Cellulose | 5.00 | MIBK | 270 | 5:1 | 1000 | 1.00 | 80% | 47% | 60 |
| 41 | Cellulose | 5.00 | MIBK | 260-280 | 5:1 | 1000 | 1.08 | 72% | 40% | 60 |
| 42 | Cellulose | 5.30 | MIBK | 280 | 5:1 | 1000 | 1.47 | 62% | 7% | 10 |

The invention has been described with reference to various specific and preferred embodiments and techniques. However, it should be understood that many variations and modifications may be made while remaining within the spirit and scope of the invention.

All publications and patents mentioned herein are hereby incorporated by reference in their entirety. The publications and patents disclosed herein are provided solely for their disclosure. Nothing herein is to be construed as an admission that the inventors are not entitled to antedate any publication and/or patent, including any publication and/or patent cited herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention claimed is:

1. A method of producing 5-hydroxymethylfurfural (HMF), comprising:
    contacting cellulose with a metal oxide catalyst at a temperature between about 260 and about 280 degrees Celsius to produce the 5-hydroxymethylfurfural (HMF) in a single reaction step wherein the metal oxide catalyst is selected from the group consisting of alumina, hafnia, titania, zirconia, and mixtures thereof.

2. The method of claim 1, wherein the contact time is less than about five minutes.

3. The method of claim 1, wherein the contact time is about two minutes.

4. The method of claim 1, further comprising contacting a solvent with the cellulose and the metal oxide catalyst.

5. The method of claim 4, the solvent comprising a ketone.

6. The method of claim 5, the ketone comprising methyl isobutyl ketone.

7. The method of claim 4, the solvent comprising an alcohol.

8. The method of claim 1, further comprising contacting cellulose with a solvent comprising methyl isobutyl ketone at a temperature of greater than 100 degrees Celsius in a solubilization chamber to form a solution prior to contacting the cellulose with the metal oxide catalyst.

* * * * *